United States Patent
Matsumoto

(10) Patent No.: US 11,759,173 B2
(45) Date of Patent: Sep. 19, 2023

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 17/557,744

(22) Filed: Dec. 21, 2021

(65) Prior Publication Data
US 2022/0110609 A1    Apr. 14, 2022

Related U.S. Application Data

(63) Continuation of application No. PCT/JP2020/026074, filed on Jul. 2, 2020.

(30) Foreign Application Priority Data

Jul. 25, 2019   (JP) .................................. 2019-136914

(51) Int. Cl.
A61B 8/00   (2006.01)
A61B 8/08   (2006.01)

(52) U.S. Cl.
CPC .......... *A61B 8/4488* (2013.01); *A61B 8/0891* (2013.01); *A61B 8/461* (2013.01); *A61B 8/52* (2013.01)

(58) Field of Classification Search
CPC .... A61B 8/58; A61B 8/54; A61B 8/52; A61B 8/4488; A61B 8/0891; A61B 8/461;
(Continued)

(56) References Cited

U.S. PATENT DOCUMENTS

2014/0187946 A1* 7/2014 Miller ............... A61B 8/54
                                                       600/443
2015/0342561 A1* 12/2015 Takeda ............ A61B 8/0841
                                                       600/443
(Continued)

FOREIGN PATENT DOCUMENTS

JP   2006-314689 A   11/2006
JP   2010-088486 A    4/2010
(Continued)

OTHER PUBLICATIONS

The extended European search report issued by the European Patent Office dated Aug. 11, 2022, which corresponds to European Patent Application No. 20843651.9.
(Continued)

*Primary Examiner* — Boniface Ngathi
*Assistant Examiner* — Zainab Mohammed Aldarraji
(74) *Attorney, Agent, or Firm* — Studebaker & Brackett PC

(57) ABSTRACT

An ultrasound diagnostic apparatus (1) includes a transmission and reception circuit (5) that causes a transducer array (2) to transmit an ultrasound beam toward the subject, and processes a reception signal output from the transducer array that has received an ultrasound echo from the subject to generate a sound ray signal; an image generation unit (6) that generates an ultrasound image on the basis of the generated sound ray signal; an image analysis unit (9) that detects the blood vessel and the insertion object by analyzing the generated ultrasound image; and a device control unit (13) that controls the transmission and reception circuit (5) such that a frame rate at which the ultrasound image is generated is adjusted, on the basis of a relative positional relationship between the detected blood vessel and the detected insertion object.

20 Claims, 6 Drawing Sheets

(58) Field of Classification Search
CPC ......... A61B 8/565; A61B 8/085; A61B 8/463; A61B 8/0841; G16H 40/60; G01S 7/5205
See application file for complete search history.

(56) References Cited

U.S. PATENT DOCUMENTS

| | | | | |
|---|---|---|---|---|
| 2016/0151039 | A1* | 6/2016 | Morikawa | A61B 8/06 600/424 |
| 2017/0049420 | A1* | 2/2017 | Shikama | A61B 8/5276 |
| 2018/0360398 | A1* | 12/2018 | Wenderow | A61M 5/007 |
| 2019/0209018 | A1* | 7/2019 | Yamamoto | A61B 10/02 |
| 2021/0038197 | A1* | 2/2021 | Liu | A61B 8/5246 |

FOREIGN PATENT DOCUMENTS

| | | |
|---|---|---|
| JP | 2012-130564 A | 7/2012 |
| JP | 2015-226572 A | 12/2015 |
| JP | 6171246 B1 | 8/2017 |
| JP | 2018-23610 A | 2/2018 |

OTHER PUBLICATIONS

International Search Report issued in PCT/JP2020/026074; dated Sep. 15, 2020.
International Preliminary Report on Patentability and Written Opinion issued in PCT/JP2020/026074; dated Jan. 25, 2022.
Csurka et al.: Visual Categorization with Bags of Keypoints, Proc. of ECCV Workshop on Statistical Learning in Computer Vision, pp. 1-16, (2004).
Krizhevsky et al.: ImageNet Classification with Deep Convolutional Neural Networks, Advances in Neural Information Processing Systems 25, pp. 1-9, (2012).

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2020/026074 filed on Jul. 2, 2020, which claims priority under 35 U.S.C. § 119(a) to Japanese Patent Application No. 2019-136914 filed on Jul. 25, 2019. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which display an insertion object to be inserted into a blood vessel of a subject, on an ultrasound image.

2. Description of the Related Art

In the related art, an ultrasound diagnostic apparatus has been known as an apparatus for obtaining an image of the inside of a subject. The ultrasound diagnostic apparatus generally comprises an ultrasound probe comprising a transducer array in which a plurality of ultrasonic transducers are arranged. In a state where the ultrasound probe is in contact with the body surface of the subject, an ultrasound beam is transmitted toward the inside of the subject from the transducer array and an ultrasound echo from the subject is received by the transducer array so that an electric signal corresponding to the ultrasound echo is acquired. Further, the ultrasound diagnostic apparatus electrically processes the obtained electric signal to generate an ultrasound image of the corresponding site of the subject.

A procedure of inserting an insertion object such as a so-called puncture needle and a catheter into the blood vessel of the subject while observing the inside of the subject using such an ultrasound diagnostic apparatus is known. In a case where the insertion object is inserted into the blood vessel, it is desirable that the frame rate at which the ultrasound image is generated is high so that an operator can grasp the motion of the insertion object and the blood vessel. For example, as disclosed in JP2010-88486A, an ultrasound diagnostic apparatus has been developed which automatically increases the frame rate at which the ultrasound image is generated, using the detection of the insertion object in the ultrasound image as a trigger.

SUMMARY OF THE INVENTION

However, in the ultrasound diagnostic apparatus in JP2010-88486A, in order to increase the frame rate using the detection of the insertion object as the trigger, for example, even in a case where the insertion object is far enough from the blood vessel, the frame rate becomes higher than necessary, so that there is a problem that power consumption is increased unnecessarily.

It is preferable that the frame rate is changed according to a relative positional relationship between the insertion object and the blood vessel, but the operator needs to concentrate on the procedure of inserting the insertion object into the blood vessel, and therefore, it is difficult to manually change the frame rate during the ultrasound diagnosis in some cases.

The present invention has been made in order to solve such a problem in the related art, and an object thereof is to provide an ultrasound diagnostic apparatus, and a control method of the ultrasound diagnostic apparatus which can automatically adjust the frame rate to an appropriate rate according to a relative positional relationship between an insertion object and a blood vessel.

In order to achieve the object, an ultrasound diagnostic apparatus according to an aspect of the present invention is an ultrasound diagnostic apparatus that displays an insertion object to be inserted into a blood vessel of a subject on an ultrasound image, and the ultrasound diagnostic apparatus comprises a transducer array; a transmission and reception circuit that causes the transducer array to transmit an ultrasound beam toward the subject, and processes a reception signal output from the transducer array that has received an ultrasound echo from the subject to generate a sound ray signal; an image generation unit that generates the ultrasound image on the basis of the sound ray signal generated by the transmission and reception circuit; an image analysis unit that detects the blood vessel and the insertion object by analyzing the ultrasound image generated by the image generation unit; and a device control unit that controls the transmission and reception circuit such that a frame rate at which the ultrasound image is generated by the image generation unit is adjusted, on the basis of a relative positional relationship between the blood vessel and the insertion object detected by the image analysis unit.

It is preferable that the device control unit controls the transmission and reception circuit such that the frame rate at which the ultrasound image is generated by the image generation unit is set to a predetermined first rate in a case where a distance between a distal end of the insertion object and the blood vessel detected by the image analysis unit exceeds a predetermined distance threshold value, and the frame rate is switched to a second rate higher than the first rate in a case where the distance between the distal end of the insertion object and the blood vessel detected by the image analysis unit is equal to or less than the predetermined distance threshold value.

Further, it is preferable that the device control unit controls the transmission and reception circuit such that the frame rate is set to a third rate in a case where the distal end of the insertion object detected by the image analysis unit is inserted into the blood vessel and a displacement amount of the distal end of the insertion object in the blood vessel within a predetermined time is equal to or less than a displacement amount threshold value.

Here, the third rate may be a rate equal to the first rate or lower than the first rate.

In this case, the device control unit controls the transmission and reception circuit such that in a case where the frame rate is the third rate, a resolution of the ultrasound image is higher than in a case where the frame rate is the second rate.

The third rate may be a rate equal to the second rate or higher than the second rate.

The image analysis unit may measure any one of a diameter, a radius, a length of an outer circumference, or an area of the detected blood vessel, and the device control unit may control the transmission and reception circuit such that the second rate becomes a higher rate as the diameter, the radius, the length of the outer circumference, or the area of the blood vessel measured by the image analysis unit is decreased.

In a case where, in the ultrasound image generated by the image generation unit, a vein into which the insertion object is to be inserted is detected as the blood vessel and an artery is detected together with the vein by the image analysis unit, the image analysis unit may measure a distance between the vein and the artery, and the device control unit may control the transmission and reception circuit such that the second rate becomes a higher rate as the distance between the vein and the artery measured by the image analysis unit is shorter.

The ultrasound diagnostic apparatus may further comprise a display device that displays the ultrasound image generated by the image generation unit; and a highlighting unit that highlights the blood vessel and the insertion object detected by the image analysis unit, on the display device.

A control method of an ultrasound diagnostic apparatus according to another aspect of the present invention is a control method of an ultrasound diagnostic apparatus that displays an insertion object to be inserted into a blood vessel of a subject on an ultrasound image, and the control method comprises causing a transducer array to transmit an ultrasound beam toward the subject, and processing a reception signal output from the transducer array that has received an ultrasound echo from the subject to generate a sound ray signal; generating the ultrasound image on the basis of the generated sound ray signal; detecting the blood vessel and the insertion object by analyzing the generated ultrasound image; and adjusting a frame rate at which the ultrasound image is generated, on the basis of a relative positional relationship between the detected blood vessel and the detected insertion object.

According to the present invention, since the ultrasound diagnostic apparatus comprises the transmission and reception circuit that causes the transducer array to transmit the ultrasound beam toward the subject, and processes the reception signal output from the transducer array that has received the ultrasound echo from the subject to generate the sound ray signal; the image generation unit that generates the ultrasound image on the basis of the sound ray signal generated by the transmission and reception circuit; the image analysis unit that detects the blood vessel and the insertion object by analyzing the ultrasound image generated by the image generation unit; and the device control unit that controls the transmission and reception circuit such that the frame rate at which the ultrasound image is generated by the image generation unit is adjusted, on the basis of the relative positional relationship between the blood vessel and the insertion object detected by the image analysis unit, it is possible to automatically adjust the frame rate to an appropriate rate according to the relative positional relationship between the insertion object and the blood vessel.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In addition, in the present specification, the terms "perpendicular" and "parallel" include a range of errors allowed in the technical field to which the present invention belongs. For example, the terms "perpendicular" and "parallel" mean a range less than ±10 degrees with respect to the strict perpendicular or parallel, and the error with respect to the strict perpendicular or parallel is preferably 5 degrees or less, and more preferably 3 degrees or less.

In the present specification, the terms "same" and "identical" include an error range generally allowed in the technical field. Further, in the present specification, in a case of referring to "all", "any", or "whole surface", the term includes an error range generally allowed in the technical field in addition to a case of 100%, and includes, for example, a case of 99% or more, a case of 95% or more, or a case of 90% or more.

First Embodiment

Figure 1:
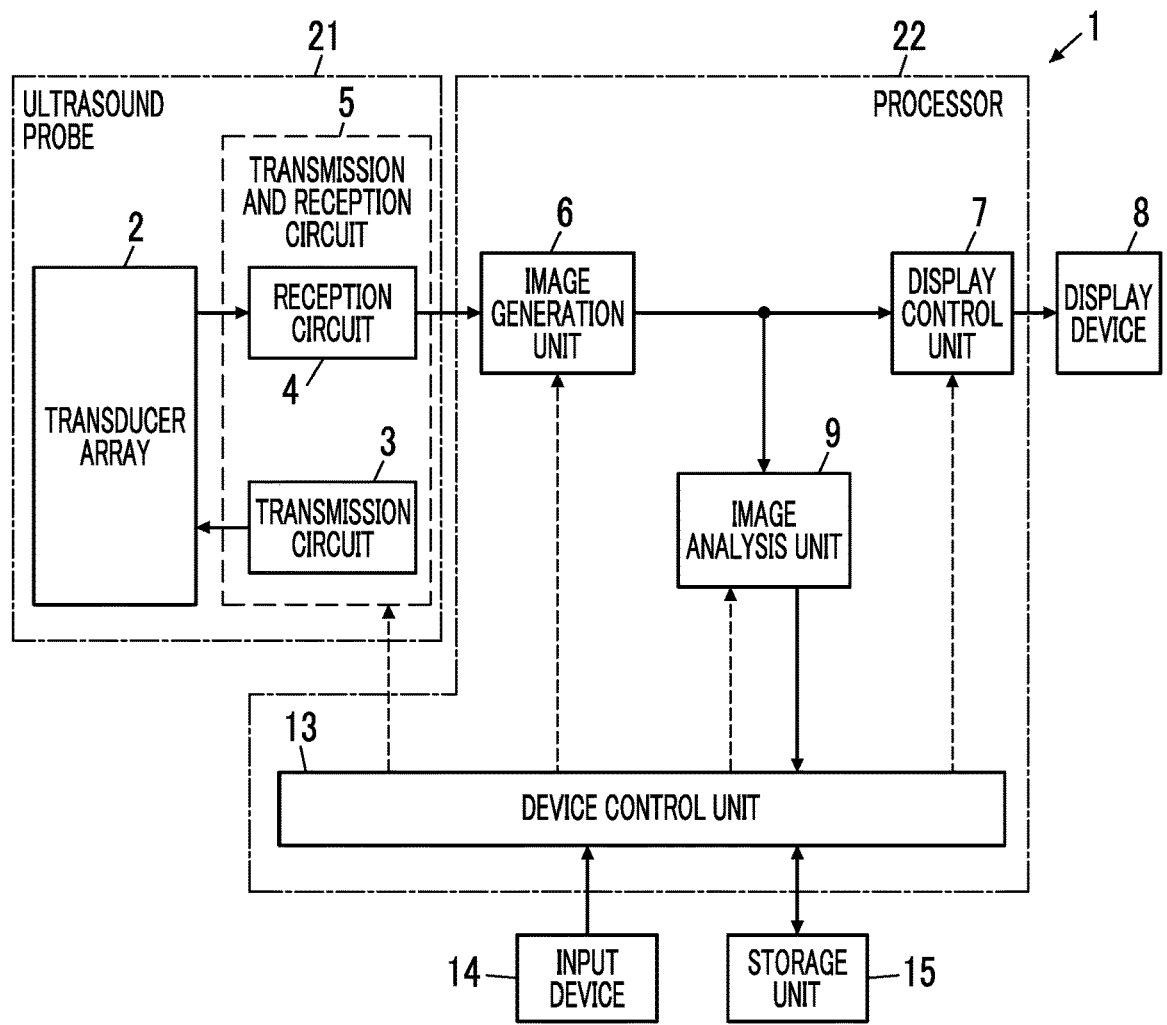
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 comprises a transducer array 2, and each of a transmission circuit 3 and a reception circuit 4 is connected to the transducer array 2. Here, the transmission circuit 3 and the reception circuit 4 constitute a transmission and reception circuit 5, and an image generation unit 6, a display control unit 7, and a display device 8 are sequentially connected to the reception circuit 4. An image analysis unit 9 is connected to the image generation unit 6.

In addition, a device control unit 13 is connected to the transmission and reception circuit 5, the image generation unit 6, the display control unit 7, and the image analysis unit 9, and an input device 14 and a storage unit 15 are connected to the device control unit 13. The device control unit 13 and the storage unit 15 are connected so as to exchange information bidirectionally.

The transducer array 2 and the transmission and reception circuit 5 are included in an ultrasound probe 21. Further, the image generation unit 6, the display control unit 7, the image analysis unit 9, and the device control unit 13 constitute a processor 22 for the ultrasound diagnostic apparatus 1.

The transducer array 2 of the ultrasound probe 21 illustrated in FIG. 1 has a plurality of transducers arranged in a one-dimensional or two-dimensional manner. According to a drive signal supplied from the transmission circuit 3, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 includes, for example, a plurality of pulse generators, and the transmission circuit 3 adjusts the amount of delay of each drive signal so that ultrasonic waves transmitted from the plurality of transducers of the transducer array 2 form an ultrasound beam on the basis of a transmission delay pattern selected according to the control signal from the device control unit 13, and supplies the obtained signals to the plurality of transducers. Thus, in a case where a pulsed or continuous-wave voltage is applied to the electrodes of the transducers of the transducer array 2, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 2 of the ultrasound probe 21. The ultrasound echo propagating toward the transducer array 2 in this manner is received by each transducer constituting the transducer array 2. In this case, each transducer constituting the transducer array 2 expands and contracts by receiving the propagating ultrasound echo to generate electric signals, and outputs the electric signals to the reception circuit 4.

Figure 2:
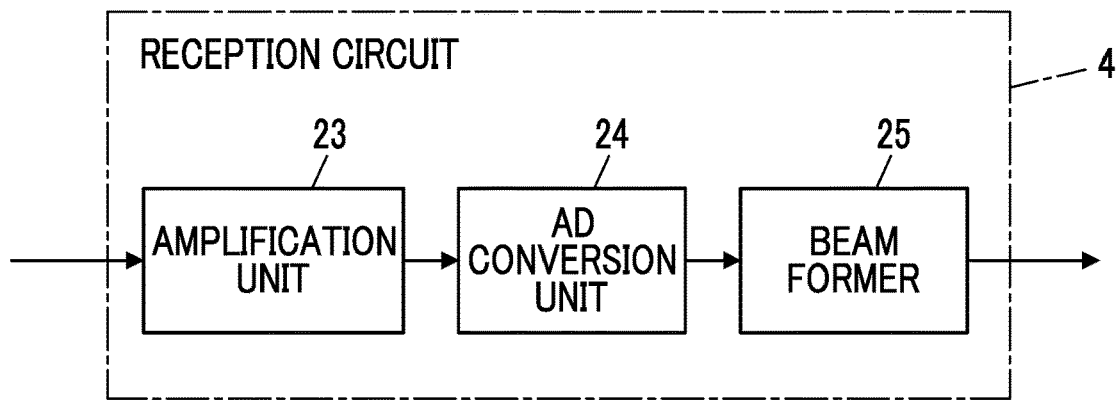
FIG. 2 is a block diagram illustrating an internal configuration of a reception circuit in the first embodiment of the present invention.

The reception circuit 4 processes the signal output from the transducer array 2 according to the control signal from the device control unit 13, and generates a sound ray signal. As illustrated in FIG. 2, the reception circuit 4 has a configuration in which an amplification unit 23, an analog digital (AD) conversion unit 24, and a beam former 25 are connected in series.

The amplification unit 23 amplifies the signal input from each transducer constituting the transducer array 2, and transmits the amplified signal to the AD conversion unit 24. The AD conversion unit 24 converts the signal transmitted from the amplification unit 23 into digital reception data, and transmits the reception data to the beam former 25. The beam former 25 performs so-called reception focusing processing in which addition is performed by giving delays to respective pieces of the reception data converted by the AD conversion unit 24 according to a sound speed distribution or a sound speed set on the basis of a reception delay pattern selected according to the control signal from the device control unit 13. Through the reception focusing processing, a sound ray signal in which each piece of the reception data converted by the AD conversion unit 24 is phased and added and the focus of the ultrasound echo is narrowed is acquired.

Figure 3:
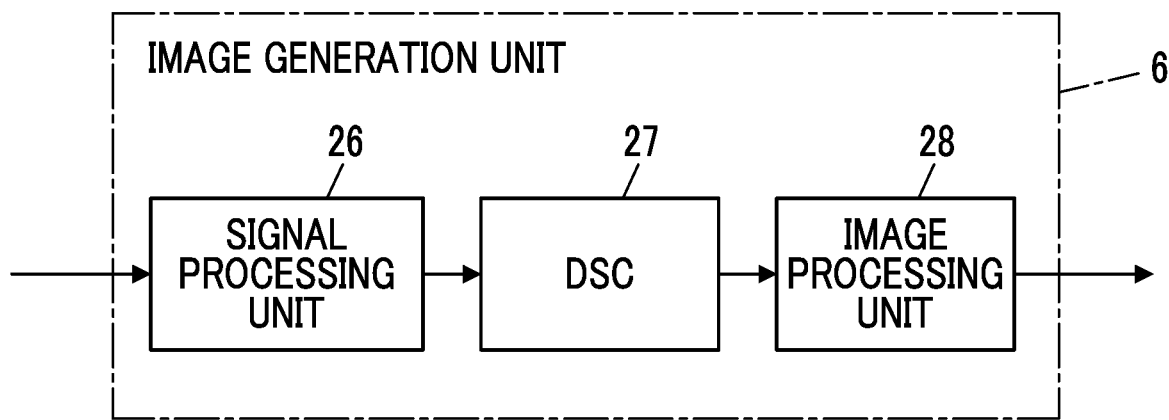
FIG. 3 is a block diagram illustrating an internal configuration of an image generation unit in the first embodiment of the present invention.

As illustrated in FIG. 3, the image generation unit 6 has a configuration in which a signal processing unit 26, a digital scan converter (DSC) 27, and an image processing unit 28 are sequentially connected in series.

The signal processing unit 26 generates a B-mode image signal, which is tomographic image information regarding tissues inside the subject, by performing, on the sound ray signal generated by the reception circuit 4, correction of the attenuation due to the distance according to the depth of the reflection position of the ultrasonic wave and then performing envelope detection processing.

The DSC 27 converts (raster conversion) the B-mode image signal generated by the signal processing unit 26 into an image signal according to a normal television signal scanning method.

The image processing unit 28 performs various kinds of necessary image processing such as gradation processing on the B-mode image signal input from the DSC 27, and then outputs the B-mode image signal to the display control unit 7 and the image analysis unit 9. In the following, the B-mode image signal subjected to the image processing by the image processing unit 28 is simply referred to as an ultrasound image.

In general, a procedure of inserting an insertion object such as a so-called puncture needle and a catheter into the blood vessel of the subject while observing the inside of the subject using the ultrasound diagnostic apparatus is known. The ultrasound diagnostic apparatus 1 according to the first embodiment of the present invention can be used by the operator in a case where such a procedure is performed.

Figure 4:
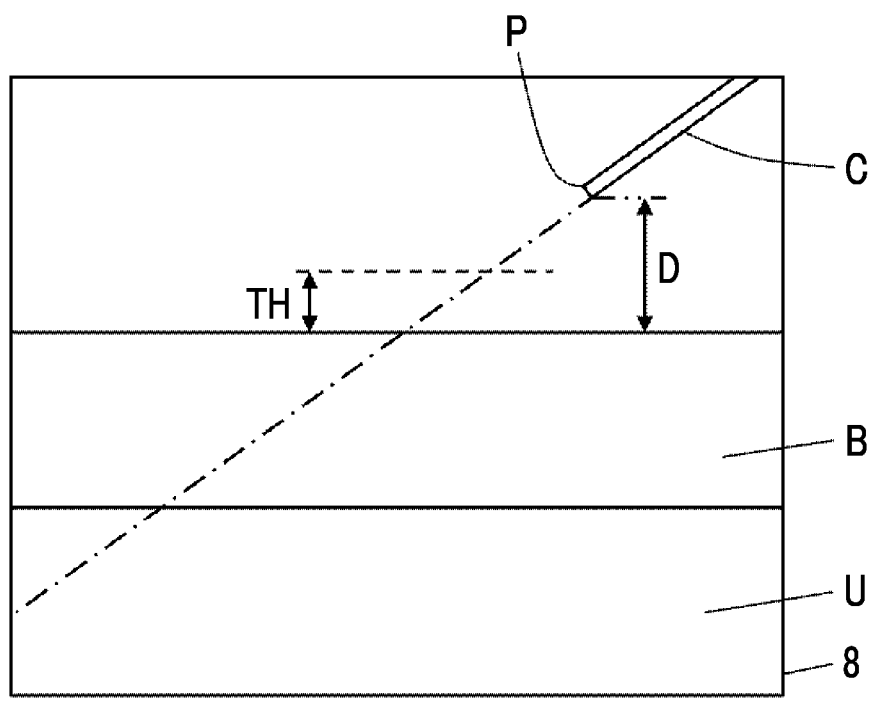
FIG. 4 is a schematic diagram of an ultrasound image indicating a state in which a distance between an insertion object and a blood vessel is greater than a distance threshold value.

The image analysis unit 9 detects a blood vessel B and an insertion object C included in an ultrasound image U, for example, as illustrated in FIG. 4 by analyzing the ultrasound image generated by the image generation unit 6. Here, the image analysis unit 9 can detect the blood vessel B and the insertion object C in the ultrasound image U using a known algorithm. For example, the image analysis unit 9 can store typical pattern data of the blood vessel B and the insertion object C in advance as a template, calculate a similarity degree for the pattern data while searching the ultrasound image U using the template, and consider that the blood vessel B and the insertion object C are present in places where the similarity degree is equal to or greater than a threshold value and is the maximum.

Further, for the calculation of the similarity degree, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

Here, FIG. 4 illustrates an example of the ultrasound image including a longitudinal cross section of the blood vessel B and a longitudinal cross section of the insertion object C. The insertion object C is inserted into the subject in the same plane as the longitudinal cross section of the blood vessel B. The longitudinal cross section of the blood vessel B refers to a cut section of the blood vessel B along a traveling direction of the blood vessel B, and the longitudinal cross section of the insertion object C refers to a cut section of the insertion object C along a direction in which the insertion object C extends.

As illustrated in FIG. 4, the image analysis unit 9 measures a distance D between a distal end P of the detected insertion object C and the blood vessel B. For example, the image analysis unit 9 can measure the shortest distance in a depth direction between the distal end P of the insertion object C and the blood vessel B, as the distance D.

Figure 5:
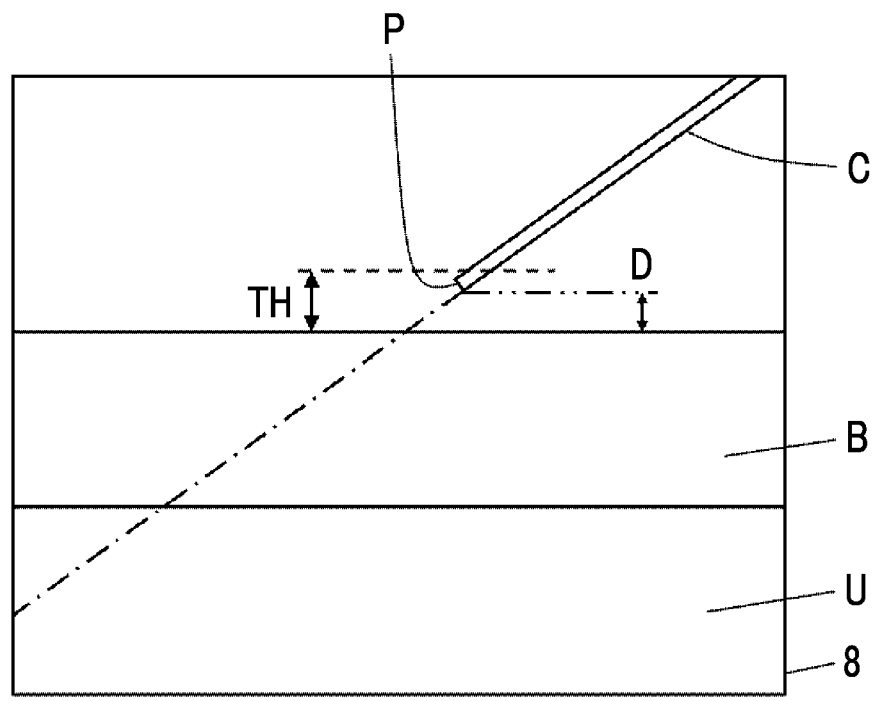
FIG. 5 is a schematic diagram of an ultrasound image indicating a state in which the distance between the insertion object and the blood vessel is equal to or less than the distance threshold value.

The device control unit 13 controls the transmission and reception circuit 5 such that the frame rate at which the image generation unit 6 generates the ultrasound image U is adjusted, on the basis of the relative positional relationship between the blood vessel B and the insertion object C detected by the image analysis unit 9. Here, in a case where the insertion object C is inserted into the blood vessel B of the subject, it is desirable that the frame rate at which the ultrasound image U is generated by the image generation unit 6 is high so that the operator can grasp the motion of the insertion object C and the blood vessel B. For example, the device control unit 13 can control the transmission and reception circuit 5 such that the frame rate at which the ultrasound image U is generated by the image generation unit 6 is set to a predetermined first rate in a case where the distance D between the distal end P of the insertion object C and the blood vessel B detected by the image analysis unit 9 exceeds a predetermined distance threshold value TH as illustrated in FIG. 4, and the frame rate at which the ultrasound image U is generated by the image generation unit 6 is switched to a second rate higher than the first rate in a case where the distance D between the distal end P of the insertion object C and the blood vessel B detected by the image analysis unit 9 is equal to or less than the predetermined distance threshold value TH as illustrated in FIG. 5.

For example, the transmission circuit 3 supplies the drive signal of which the amount of delay is adjusted to the plurality of transducers of the transducer array 2 such that the ultrasound beam converges on the set scan line, but the device control unit 13 decreases the number of scan lines used for generating the ultrasound image U of one frame, that is, the number of sound ray signals corresponding to the ultrasound image U of one frame by controlling the transmission circuit 3 such that the number of scan lines to which the ultrasound beam is transmitted is decreased, and thereby can switch the frame rate from the first rate to the second rate. It is conceivable that, in a case where the number of sound ray signals corresponding to the ultrasound image U of one frame is decreased, the resolution of the generated ultrasound image U is decreased while the frame rate is increased, but, for example, the device control unit 13 increases the number of pieces of reception data phased and added for generating the sound ray signal by controlling the transmission and reception circuit 5 such that the number of scan lines for which the reception focusing processing is performed instead of decreasing the number of scan lines to which the ultrasound beam is transmitted, and thereby can increase the resolution of the ultrasound image U to be generated even after the frame rate is switched to the second rate.

Figure 6:
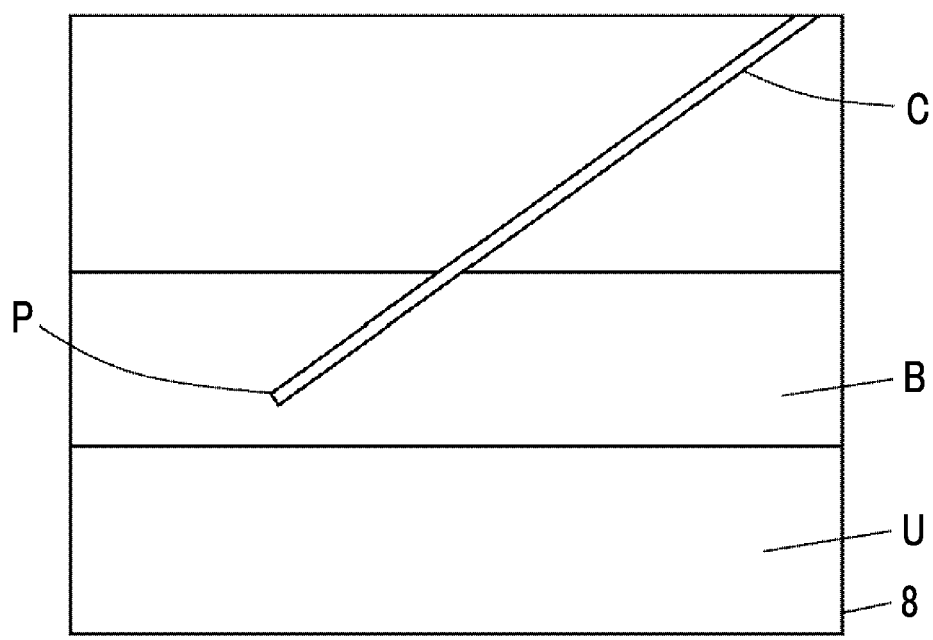
FIG. 6 is a schematic diagram of an ultrasound image indicating a state in which a distal end of the insertion object is inserted into the blood vessel.

The device control unit 13 controls the transmission and reception circuit 5 such that the frame rate at which the ultrasound image U is generated by the image generation unit 6 is set to a third rate in a case where the distal end P of the insertion object C detected by the image analysis unit 9 is inserted into the blood vessel B and a displacement amount of the distal end P of the insertion object C in the blood vessel B within a predetermined time is equal to or less than a displacement amount threshold value, as illustrated in FIG. 6.

Here, the displacement amount of the distal end P of the insertion object C in the blood vessel B within the predetermined time refers to a linear distance between a position of the distal end P of the insertion object C in the ultrasound image U first generated within the predetermined time and a position of the distal end P of the insertion object C in the ultrasound image U newly generated within the predetermined time, in a state where the distal end P of the insertion object C is positioned in the blood vessel B. For example, the image analysis unit 9 can measure the displacement amount of the distal end P of the insertion object C in the blood vessel B within the predetermined time by analyzing a plurality of ultrasound images U consecutively generated by the image generation unit 6. The device control unit 13 determines whether the displacement amount of the distal end P of the insertion object C within the predetermined time, which is measured by the image analysis unit 9 in this manner, is equal to or less than the displacement amount threshold value.

The third rate can be set to a rate equal to the first rate or lower than the first rate. That is, the third rate can be set to a rate lower than the second rate. In this case, the device control unit 13 can control the transmission and reception circuit 5 such that in a case where the frame rate is the third rate, the resolution of the ultrasound image U is higher than in a case where the frame rate is the second rate. In this case, the operator can accurately grasp the position of the distal end P of the insertion object C positioned in the blood vessel B of the subject.

Further, the third rate can also be set to a rate equal to the second rate or higher than the second rate. In this case, the operator can accurately grasp the motion of the distal end P of the insertion object C positioned in the blood vessel B.

In addition, the device control unit 13 controls each unit of the ultrasound diagnostic apparatus 1 on the basis of a program stored in advance in the storage unit 15 or the like and the operator's input operation through the input device 14.

The display control unit 7 performs predetermined processing on the ultrasound image U generated by the image generation unit 6 and displays the ultrasound image U on the display device 8, under the control of the device control unit 13.

The display device 8 is for displaying the ultrasound image U, the instruction to the operator by the notification unit 12, and the like under the control of the display control unit 7, and includes a display device such as a liquid crystal display (LCD), or an organic electroluminescence (EL) display.

The input device 14 is for the operator to perform an input operation, and can be configured to comprise a keyboard, a mouse, a trackball, a touchpad, a touch panel, and the like.

The storage unit 15 stores a control program and the like of the ultrasound diagnostic apparatus 1, and recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The processor 22 having the image generation unit 6, the display control unit 7, the image analysis unit 9, and the device control unit 13 is configured by a central processing unit (CPU) and a control program for causing the CPU to execute various kinds of processing, but the processor 22 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 6, the display control unit 7, the image analysis unit 9, and the device control unit 13 of the processor 22 can also be configured by being integrated partially or entirely into one CPU or the like.

Figure 7:
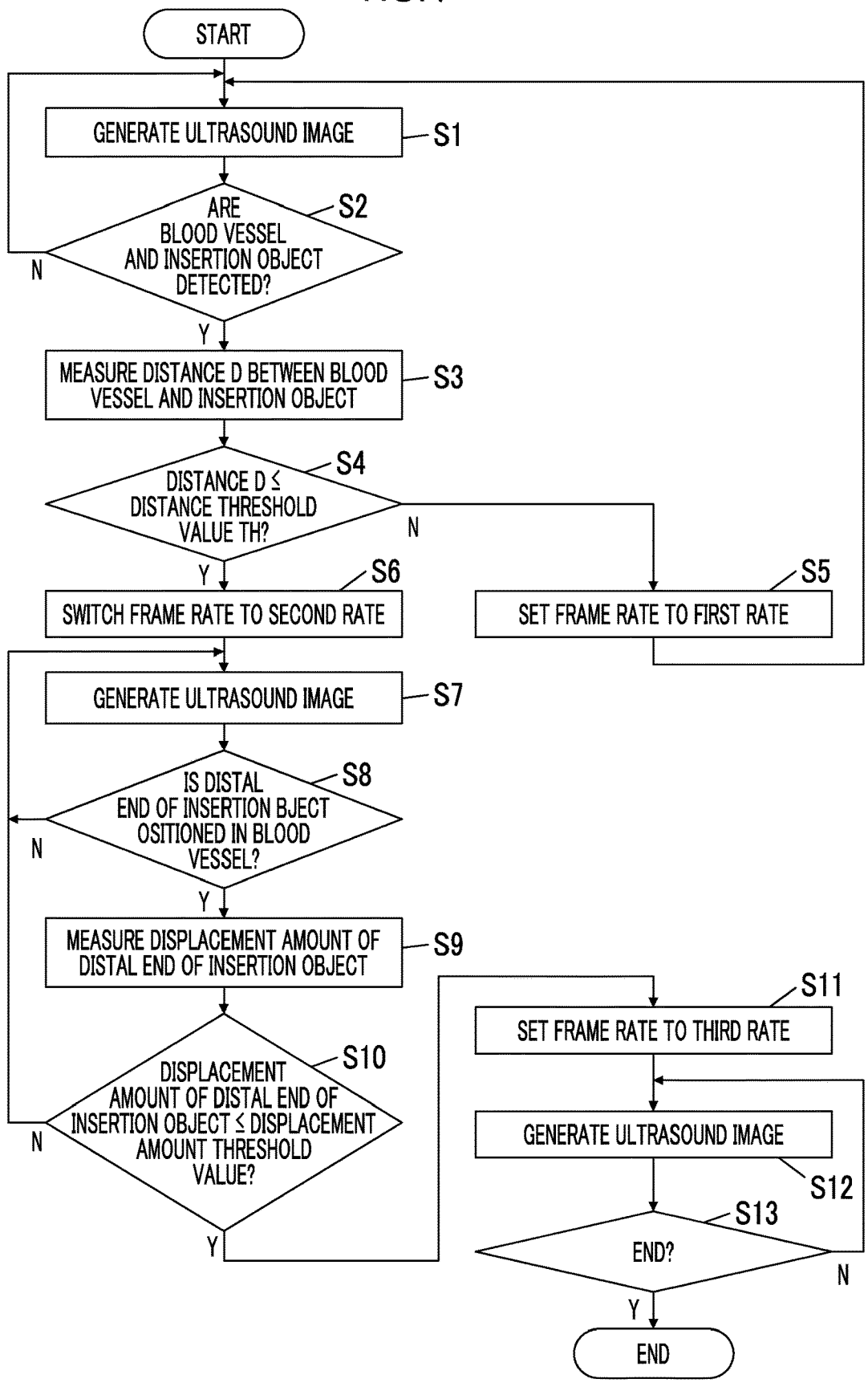
FIG. 7 is a flowchart illustrating an operation of the ultrasound diagnostic apparatus according to the first embodiment of the present invention.

In the following, the operation of the ultrasound diagnostic apparatus 1 in the first embodiment will be described in detail using the flowchart illustrated in FIG. 7.

First, in Step S1, the ultrasound image U in which at least the blood vessel B of the subject is imaged is generated, and the generated ultrasound image U is displayed on the display device 8. In this case, the ultrasound probe 21 is brought into contact with the body surface of the subject by the operator, an ultrasound beam is transmitted from the plurality of transducers of the transducer array 2 according to the drive signal from the transmission circuit 3, and the reception signal is output to the reception circuit 4 from each transducer which has received the ultrasound echo from the subject. The reception signal received by the reception circuit 4 is amplified in the amplification unit 23, is subjected to the AD conversion in the AD conversion unit 24, and is phased and added in the beam former 25, and thereby the sound ray signal is generated. The sound ray signal is subjected to the envelope detection processing by the signal processing unit 26 to become the B-mode image signal in the image generation unit 6, and is output to the display control unit 7 via the DSC 27 and the image processing unit 28, and the ultrasound image U is displayed on the display device 8 under the control of the display control unit 7 as illustrated in FIG. 4.

Next, in Step S2, the operator inserts the insertion object C into the subject while checking the ultrasound images U consecutively generated and displayed on the display device 8. Here, the image analysis unit 9 performs processing of detecting the blood vessel B and the insertion object C such as a puncture needle and a catheter by analyzing the generated ultrasound image U. In this case, the image analysis unit 9 can detect the blood vessel B and the insertion object C by using, for example, a known algorithm such as template matching, a machine learning method, a general image recognition method using deep learning or the like. In a case where the blood vessel B and the insertion object C are not detected in Step S2, the processing returns to Step S1, the ultrasound image U is newly generated, and the processing of detecting the blood vessel B and the insertion object C is performed again in subsequent Step S2. In a case where the blood vessel B and the insertion object C are detected in Step S2, the processing proceeds to Step S3.

In Step S3, the image analysis unit 9 measures the distance D between the insertion object C and the blood vessel B of the subject detected in Step S2, as illustrated in FIG. 4. For example, the image analysis unit 9 can measure the shortest distance in the depth direction between the distal end P of the insertion object C and the blood vessel B, as the distance D.

In Step S4, the device control unit 13 determines whether the distance D between the blood vessel B and the insertion object C measured in Step S3 is equal to or less than the distance threshold value TH. In a case where the distance D between the blood vessel B and the insertion object C is greater than the distance threshold value TH as illustrated in FIG. 4, the processing proceeds to Step S5.

In Step S5, the device control unit 13 controls the transmission and reception circuit 5 such that the frame rate at which the ultrasound image U is generated by the image generation unit 6 is set to the first rate, and the processing returns to Step S2. Here, the first rate may be equal to or may be different from the frame rate used in a case where the ultrasound image U is generated in Step S1 to Step S4. In a case where the first rate is a rate higher than the frame rate used in a case where the ultrasound image U is generated in Step S1 to Step S4, the operator can more accurately grasp the motion of the insertion object C inserted into the subject by checking the ultrasound image U.

In a case where Step S5 is completed, the processing returns to Step S1, and the ultrasound image U is newly generated. Since the insertion object C and the blood vessel B of the subject are included in the ultrasound image U generated here, the blood vessel B and the insertion object C are detected in Step S2, and the processing proceeds to Step S3. In Step S3, the blood vessel B of the subject and the insertion object C are detected and the distance D between the detected blood vessel B and insertion object C is measured on the basis of the newly generated ultrasound image U, and in Step S4, it is determined whether the measured distance D is equal to or less than the distance threshold value TH. In a case where it is determined that the distance D between the blood vessel B and the insertion object C is equal to or less than the distance threshold value TH as illustrated in FIG. 5, the processing proceeds to Step S6.

In Step S6, the device control unit 13 controls the transmission and reception circuit 5 such that the frame rate at which the ultrasound image U is generated is switched from the first rate to the second rate greater than the first rate. In this case, for example, the device control unit 13 controls the transmission and reception circuit 5 such that the number of scan lines used for generating the ultrasound image U of one frame is decreased, that is, the number of sound ray signals corresponding to the ultrasound image U of one frame is decreased, and thereby can switch the frame rate from the first rate to the second rate. Since the second rate is greater than the first rate, the operator can more accurately grasp the motion of the insertion object C and the motion of the blood vessel B in a case where the insertion object C is inserted into the blood vessel B, and it is possible to improve the accuracy of inserting the insertion object C into the blood vessel B.

Here, it is conceivable that, in a case where the number of sound ray signals corresponding to the ultrasound image U of one frame is decreased, the resolution of the generated ultrasound image U is decreased while the frame rate is increased, but, for example, the device control unit 13 increases the number of pieces of reception data phased and added for generating the sound ray signal, and thereby can increase the resolution of the ultrasound image U to be generated even after the frame rate is switched to the second rate.

In a case where the frame rate is switched to the second rate in this manner, the processing proceeds to Step S7, the ultrasound image U is newly generated at the second rate.

In subsequent Step S8, the image analysis unit 9 determines whether the distal end P of the insertion object C is positioned in the blood vessel B by analyzing the ultrasound image U. For example, the image analysis unit 9 can determine that the distal end P of the insertion object C is positioned in the blood vessel B by recognizing that the distal end P of the insertion object C is positioned in the blood vessel B by using, for example, a known algorithm such as template matching, a machine learning method, a general image recognition method using deep learning or the like. Further, for example, the image analysis unit 9 measures the distance D between the blood vessel B and the distal end P of the insertion object C in the same manner as in Step S3, and in a case where the measured distance D is zero, the image analysis unit 9 can determine that the distal end P of the insertion object C is positioned in the blood vessel B.

In a case where it is determined in Step S8 that the distal end P of the insertion object C is positioned outside the blood vessel B, the processing returns to Step S7, the ultrasound image U is newly generated, and in subsequent Step S8, it is determined again whether the distal end P of the insertion object C is positioned in the blood vessel B. In a case where it is determined in Step S8 that the distal end P of the insertion object C is positioned in the blood vessel B, the processing proceeds to Step S9.

In Step S9, the image analysis unit 9 measures the displacement amount of the distal end P of the insertion object C in the blood vessel B within the predetermined time. For example, the image analysis unit 9 can measure the displacement amount of the distal end P of the insertion object C in the blood vessel B within the predetermined time by analyzing a plurality of ultrasound images U consecutively generated by the image generation unit 6.

In subsequent Step S10, the device control unit 13 determines whether the displacement amount of the distal end P of the insertion object C measured in Step S9 is equal to or less than the displacement amount threshold value. In a case where the displacement amount of the distal end P of the insertion object C measured in Step S9 is greater than the displacement amount threshold value, it is determined that the position of the distal end P of the insertion object C is not stable in the blood vessel B, the processing returns to Step S7, and the ultrasound image U is newly generated. Since the distal end P of the insertion object C is positioned in the blood vessel B in the ultrasound image U generated here, it is determined in Step S8 that the distal end P of the insertion object C is positioned in the blood vessel B, and the processing proceeds to Step S9. In Step S9, the displacement amount of the distal end P of the insertion object C is newly measured, and in Step S10, it is determined whether the newly measured displacement amount of the distal end P of the insertion object C is equal to or less than the displacement amount threshold value.

In a case where it is determined that the displacement amount of the distal end P of the insertion object C is equal to or less than the displacement amount threshold value, it is determined that the position of the distal end P of the insertion object C is stable in the blood vessel B, and the processing proceeds to Step S11.

In Step S11, the device control unit 13 controls the transmission and reception circuit 5 such that the frame rate at which the ultrasound image U is generated by the image generation unit 6 is set to the third rate.

Here, the third rate can be set to a rate equal to the first rate or lower than the first rate. That is, the third rate can be set to a rate lower than the second rate. In this case, the device control unit 13 can control the transmission and reception circuit 5 such that in a case where the frame rate is the third rate, the resolution of the ultrasound image U is higher than in a case where the frame rate is the second rate. In this case, the operator can accurately grasp the position of the insertion object C positioned in the blood vessel B of the subject, and can dispose the insertion object C at an appropriate position in the blood vessel B.

Further, the third rate can also be set to a rate equal to the second rate or higher than the second rate. In this case, the operator can accurately grasp the motion of the insertion object C positioned in the blood vessel B, and can prevent the distal end P of the insertion object C from being brought into contact with a so-called posterior vascular wall positioned in a deep portion.

The value of the third rate can be set in advance by the operator through the input device 14, for example.

In this manner, in a case where the processing of Step S10 is completed, the processing proceeds to Step S12, and the ultrasound image U is newly generated at the third rate. In a case where the ultrasound image U is generated at the third rate, the operator performs a procedure of moving the insertion object C or the like such that the insertion object C is disposed at an appropriate position in the blood vessel B.

In subsequent Step S13, it is determined whether to end the operation of the ultrasound diagnostic apparatus 1. For example, in a case where an instruction to end the operation of the ultrasound diagnostic apparatus 1 is input by the operator through the input device 14 or the like, it is determined that the operation of the ultrasound diagnostic apparatus 1 is to be ended, and in a case where an instruction to end the operation of the ultrasound diagnostic apparatus 1 is not input, it is determined that the operation of the ultrasound diagnostic apparatus 1 is not to be ended. In a case where it is determined that the operation of the ultrasound diagnostic apparatus 1 is not to be ended, the processing returns to Step S12, and the ultrasound image U is newly generated. In a case where it is determined that the operation of the ultrasound diagnostic apparatus 1 is to be ended, the operation of the ultrasound diagnostic apparatus 1 is ended.

As described above, with the ultrasound diagnostic apparatus 1 according to the first embodiment of the present invention, since the insertion object C inserted into the subject and the blood vessel B of the subject are detected by analyzing the ultrasound image U and the transmission and reception circuit 5 is automatically controlled to adjust the frame rate at which the ultrasound image U is generated by the image generation unit 6, on the basis of the relative positional relationship between the detected insertion object C and blood vessel B, the operator can automatically adjust the frame rate to an appropriate rate according to the relative positional relationship between the insertion object C and the blood vessel B while performing a procedure of inserting the insertion object C into the blood vessel B. Thereby, it is possible to improve the accuracy with which the operator inserts the insertion object C into the blood vessel B of the subject, and even in a state where the distal end P of the insertion object C is positioned in the blood vessel B, the operator can dispose the distal end P of the insertion object C at an appropriate position.

It is described that the image analysis unit 9 measures the distance D between the distal end P of the insertion object C and the blood vessel B by analyzing the ultrasound image U including the longitudinal cross sections of the blood vessel B and the insertion object C, but the image analysis unit 9 can measure the distance D between the distal end P of the insertion object C and the blood vessel B by analyzing the ultrasound image U including the cross sections of the blood vessel B and the insertion object C.

In general, in the ultrasound image U, the cross section of the insertion object such as a puncture needle and a catheter is depicted to have a point shape with high brightness, and it is known that since the distal end of the insertion object has a sharp shape, a so-called acoustic shadow is less likely to occur on a deeper side than the distal end of the insertion object. On the other hand, since a so-called shaft portion closer to the proximal end side than the distal end of the insertion object is thicker than the distal end, an acoustic shadow is likely to occur on a deeper side than the shaft portion of the insertion object. Therefore, in a case where an acoustic shadow does not occur on the deep side of the insertion object C, it is determined that the insertion object C depicted in the ultrasound image U is the distal end P thereof, the image analysis unit 9 can measure the distance D between the distal end P of the insertion object C and the blood vessel B.

Here, the cross section of the blood vessel B refers to a cut section of the blood vessel B by a plane orthogonal to the traveling direction of the blood vessel B, and the cross section of the insertion object C refers to a cut section of the insertion object C by a plane orthogonal to the direction in which the insertion object C extends.

As the insertion object C to be inserted into the subject, a so-called echogenic needle in which a groove is formed on the outer peripheral portion of the puncture needle so that ultrasonic waves are easily reflected can be used. In a case where such a puncture needle is used, for example, since the ultrasonic waves are easily reflected in the groove formed on the outer peripheral portion of the puncture needle, a location where the puncture needle is present in the ultrasound image U becomes high brightness, and detecting the puncture needle becomes easy. However, in the ultrasound diagnostic apparatus 1 of the first embodiment of the present invention, a normal puncture needle in which no groove is formed on the outer peripheral portion can also be used as the insertion object C to be inserted into the subject.

In a case where the insertion object C is inserted into the blood vessel B of the subject, normally, the larger the diameter of the blood vessel B, the easier it is to insert the insertion object C into the blood vessel B, and the smaller the diameter of the blood vessel B, the more difficult it is to insert the insertion object C into the blood vessel B. Therefore, the image analysis unit 9 measures the diameter of the detected blood vessel B by analyzing the ultrasound image U, and the device control unit 13 can control the transmission and reception circuit 5 such that the second rate becomes a higher rate as the diameter of the blood vessel B measured by the image analysis unit 9 is decreased. In this case, even in a case where the diameter of the detected blood vessel B is small, since the operator can easily grasp the motions of the insertion object C and the blood vessel B by checking the ultrasound image U, it is possible to improve the accuracy of inserting the insertion object C into the blood vessel B. Further, the image analysis unit 9 can measure, for example, the radius, the length of the outer circumference, or the area of the blood vessel B instead of measuring the diameter of the blood vessel B. In this case, the image analysis unit 9 can control the transmission and reception circuit 5 such that the second rate becomes a higher rate as the measured radius, length of the outer circumference, or area of the blood vessel B is decreased.

In a case where the insertion object C is to be inserted into the vein positioned near the artery, the device control unit 13 can control the transmission and reception circuit 5 such that the second rate becomes a high rate. In this case, the image analysis unit 9 detects the blood vessel B of the subject by distinguishing the vein and the artery, and in a case where the vein into which the insertion object C is to be inserted is detected as the blood vessel B and the artery is detected together with the vein, the image analysis unit 9 can measure the linear distance between the detected vein and artery. Further, the device control unit 13 can control the transmission and reception circuit 5 such that the second rate becomes a higher rate as the distance between the vein and the artery measured by the image analysis unit 9 is shorter.

In this case, even in a case where the vein into which the insertion object C is to be inserted is position near the artery, the operator can easily grasp the motion of the insertion object C by checking the ultrasound image U, and therefore, it is possible to prevent the insertion object C from being erroneously inserted into the artery.

For example, in a case where the distance between the artery and the distal end P of the insertion object C inserted into the subject is equal to or less than a certain value, the device control unit 13 can display a message indicating a warning to the operator, such as "do not pierce the artery with the insertion object", on the display device 8. Although not illustrated, the ultrasound diagnostic apparatus 1 comprises a speaker, and the device control unit 13 can control the speaker to emit a warning sound or voice warning so that the insertion object C is not inserted into the artery.

Figure 8:
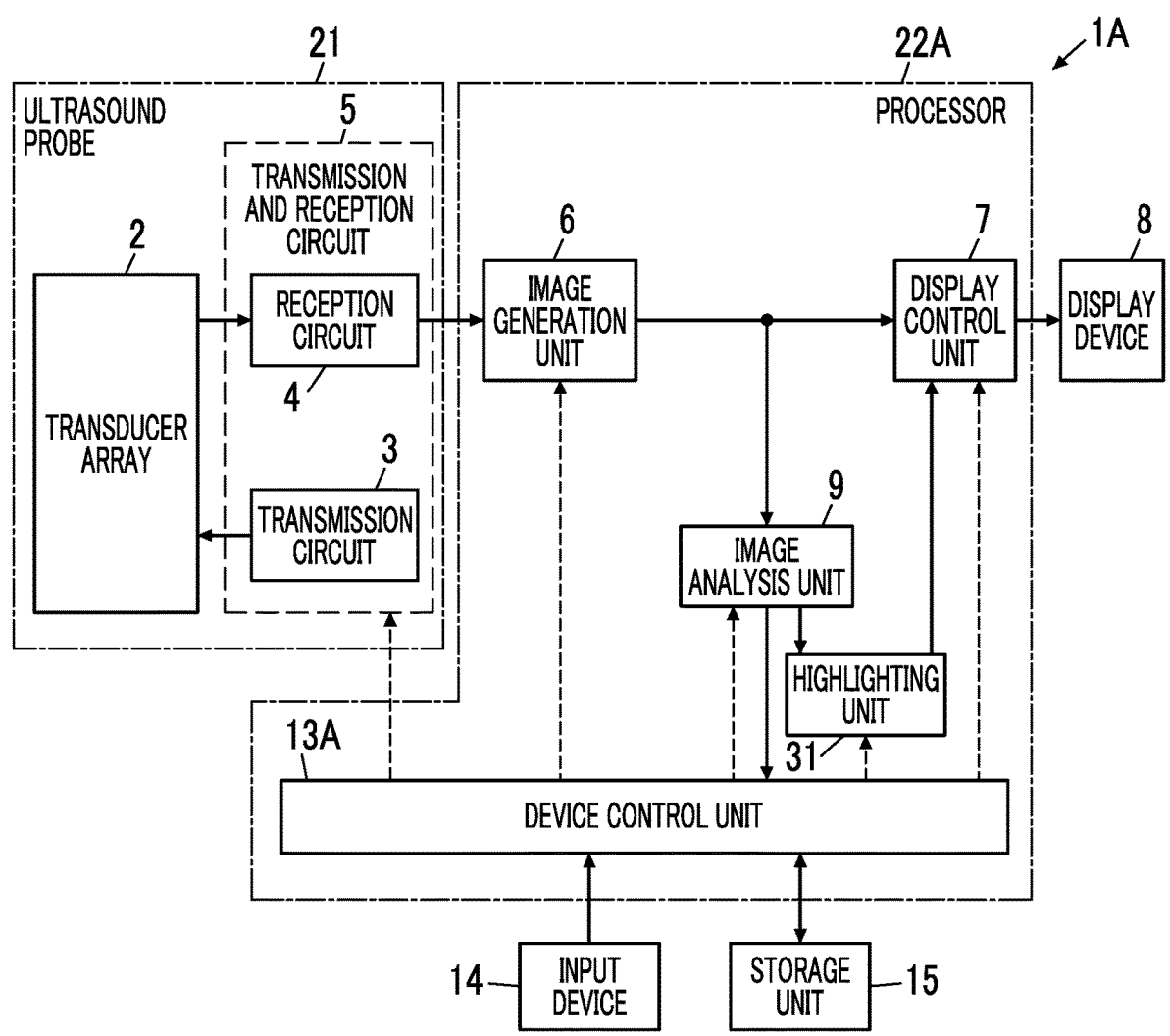
FIG. 8 is a block diagram of an ultrasound diagnostic apparatus according to a modification example of the first embodiment of the present invention.

FIG. 8 illustrates a configuration of an ultrasound diagnostic apparatus 1A according to a modification example of the first embodiment of the present invention. The ultrasound diagnostic apparatus 1A is obtained by adding a highlighting unit 31 to the ultrasound diagnostic apparatus 1 illustrated in FIG. 1, comprising a device control unit 13A instead of the device control unit 13, and comprising a processor 22A instead of the processor 22. In the ultrasound diagnostic apparatus 1A, the highlighting unit 31 is connected to the image analysis unit 9, and the display control unit 7 and the device control unit 13A is connected to the highlighting unit 31.

The highlighting unit 31 highlights the blood vessel B and the insertion object C detected by the image analysis unit 9, on the display device 8. For example, although not illustrated, as the highlighting, the highlighting unit 31 can display the detected blood vessel B and insertion object C with a different color from that of a portion other than the blood vessel B and the insertion object C in the ultrasound image U, on the display device 8. Further, for example, although not illustrated, as the highlighting, the highlighting unit 31 can display texts on the display device 8 by disposing the text indicating a blood vessel near the detected blood vessel B, and disposing the text indicating an insertion object near the insertion object C.

In this manner, since the blood vessel B and the insertion object C detected by the image analysis unit 9 are highlighted on the display device 8, the operator can easily check the detected blood vessel B and insertion object C, and it is possible to improve the accuracy of inserting the insertion object C into the blood vessel B.

Further, the transmission and reception circuit 5 is included in the ultrasound probe 21, but may be provided outside the ultrasound probe 21. In such a case, similarly to the case where the transmission and reception circuit 5 is included in the ultrasound probe 21, the transmission and reception circuit 5 can cause the transducer array 2 to transmit the ultrasound beam toward the subject, and process the reception signal output from the transducer array 2 that has received the ultrasound echo from the subject.

Further, the beam former 25 that performs so-called reception focusing processing is included in the reception circuit 4, but can be included in the image generation unit 6, for example. Also in this case, similarly to the case where the beam former 25 is included in the reception circuit 4, the ultrasound image U is generated by the image generation unit 6.

An example in which the frame rate at which the ultrasound image U is generated by the image generation unit 6 is increased by decreasing the number of scan lines used for generating the ultrasound image U of one frame has been described, but the method of increasing the frame rate at which the ultrasound image U is generated by the image generation unit 6 is not limited thereto. For example, the transmission circuit 3 supplies the drive signal of which the amount of delay is adjusted to the plurality of transducers of the transducer array 2 so that the ultrasound beam converges on each of a plurality of focuses set in the depth direction, but the device control unit 13 controls the transmission circuit 3 to decrease the number of set focuses, and can increase the frame rate at which the ultrasound image U is generated by the image generation unit 6 by reducing the time required for transmitting the ultrasonic waves.

The device control unit 13 can control the transmission and reception circuit 5 such that a depth range of the ultrasound image U, that is, the depth of field is shallow to shorten the transmission interval of the ultrasonic waves, and can increase the frame rate at which the ultrasound image U is generated by the image generation unit 6.

Further, the device control unit 13 controls the transmission and reception circuit 5 such that the visual field width is narrowed while the interval of the scan line is maintained, to decrease the number of times of transmitting and receiving the ultrasonic waves and decrease the number of scan lines used for generating the ultrasound image U, and thereby can increase the frame rate.

In general, a so-called tissue harmonic imaging (THI) method is known in which the ultrasound image is generated by extracting a harmonic component, which is a non-linear component, from a signal corresponding to an ultrasound echo received by the transducer array by using the non-linearity of the signal obtained by the ultrasound echo reflected by the tissue in the subject, in order to improve the resolution of the ultrasound image to be generated. Further, as the tissue harmonic imaging method, a pulse inversion method is known in which a first ultrasonic pulse and a second ultrasonic pulse of which phases are inverted from each other on the same scan line are sequentially transmitted into the subject, and the harmonic component is extracted by removing the fundamental wave component, which is a linear component, from the reception signal by adding the reception signal corresponding to the first ultrasonic pulse and the reception signal corresponding to the second ultrasonic pulse to each other.

Therefore, in a case where the ultrasound image U is generated using the pulse inversion method, for example, the device control unit 13 controls the transmission and reception circuit 5 and the image generation unit 6 such that the ultrasound image U is generated using the fundamental wave component of the reception signal by a normal method that does not use the pulse inversion method, and thereby can increase the frame rate at which the ultrasound image U is generated by the image generation unit 6.

As a kind of tissue harmonic imaging method, in addition to the pulse inversion method, a so-called filter method is known in which the fundamental wave component is removed from the reception signal and the harmonic component is extracted by applying a frequency filter to the reception signal. Therefore, in a case where the ultrasound image U is generated using the pulse inversion method, the device control unit 13 controls the transmission and reception circuit 5 and the image generation unit 6 such that the ultrasound image U is generated using, for example, the filter method, and thereby can increase the frame rate at which the ultrasound image U is generated by the image generation unit 6.

Second Embodiment

The ultrasound diagnostic apparatus 1 of the first embodiment has the configuration in which the display device 8, the input device 14, and the ultrasound probe 21 are directly connected to the processor 22, but, for example, the display device 8, the input device 14, the ultrasound probe 21, and the processor 22 can be indirectly connected to each other via the network.

Figure 9:
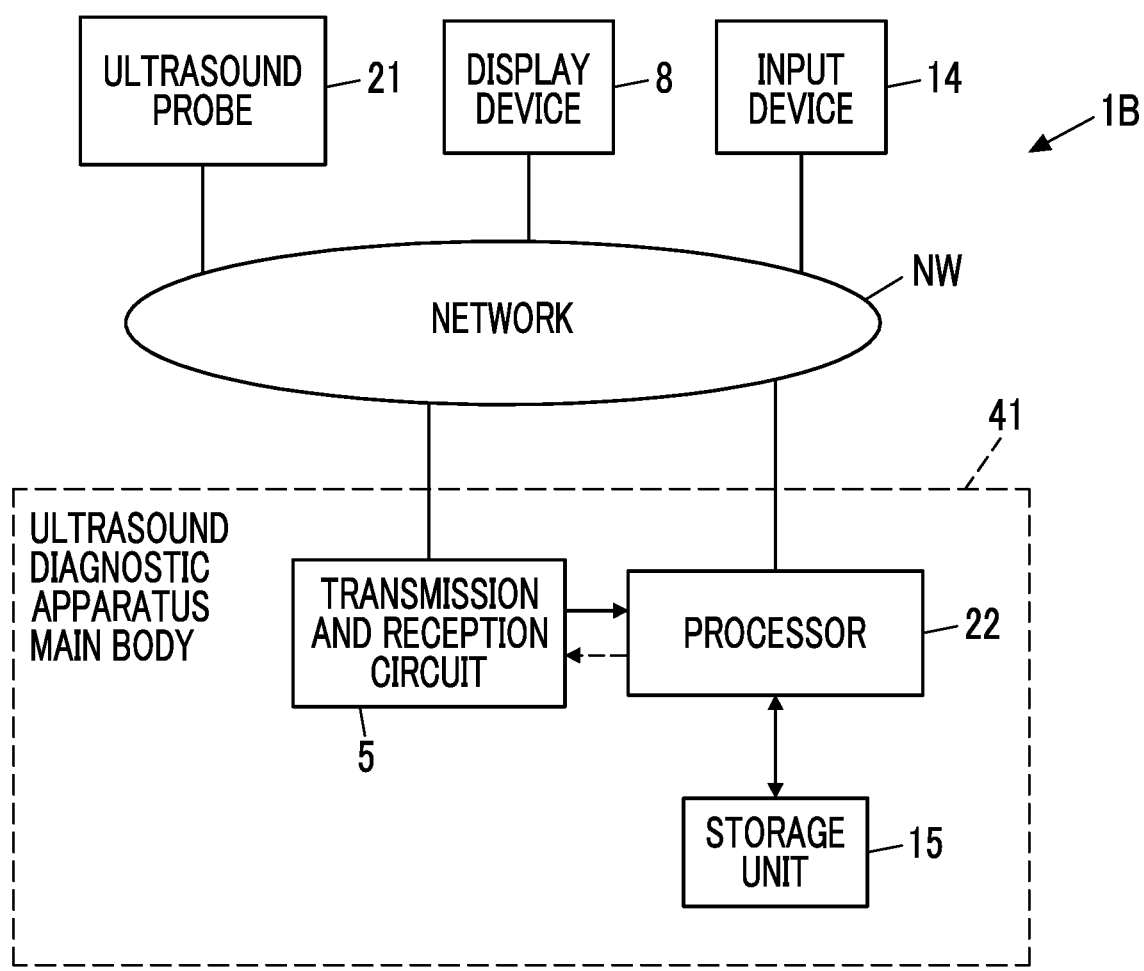
FIG. 9 is a block diagram illustrating an ultrasound diagnostic apparatus according to a second embodiment of the present invention.

As illustrated in FIG. 9, in an ultrasound diagnostic apparatus 1B in a second embodiment, the display device 8, the input device 14, and the ultrasound probe 21 are connected to an ultrasound diagnostic apparatus main body 41 via a network NW. The ultrasound diagnostic apparatus main body 41 is obtained by excluding the display device 8, the input device 14, and the ultrasound probe 21 in the ultrasound diagnostic apparatus 1 of the first embodiment illustrated in FIG. 1, and is constituted by the transmission and reception circuit 5, the storage unit 15, and the processor 22.

Even in a case where the ultrasound diagnostic apparatus 1B has such a configuration, similarly to the ultrasound diagnostic apparatus 1 of the first embodiment, since the insertion object C inserted into the subject and the blood vessel B of the subject are detected by analyzing the ultrasound image U and the transmission and reception circuit 5 is automatically controlled to adjust the frame rate at which the ultrasound image U is generated by the image generation unit 6, on the basis of the relative positional relationship between the detected insertion object C and blood vessel B, the operator can adjust the frame rate to an appropriate rate according to the relative positional relationship between the insertion object C and the blood vessel B while performing a procedure of inserting the insertion object C into the blood vessel B. Thereby, it is possible to improve the accuracy with which the operator inserts the insertion object C into the blood vessel B of the subject, and even in a state where the distal end P of the insertion object C is positioned in the blood vessel B, the operator can dispose the distal end P of the insertion object C at an appropriate position.

Further, since the display device 8, the input device 14, and the ultrasound probe 21 are connected to the ultrasound diagnostic apparatus main body 41 via the network NW, the ultrasound diagnostic apparatus main body 41 can be used as a so-called remote server. Thereby, for example, since the operator can perform a diagnosis of the subject by preparing the display device 8, the input device 14, and the ultrasound probe 21 at the operator's hand, it is possible to improve the convenience in a case of the ultrasound diagnosis.

Further, in a case where a portable thin computer, for example, a so-called tablet, is used as the display device 8 and the input device 14, it is possible for the operator to more easily perform the ultrasound diagnosis of the subject, and it is possible to further improve the convenience in a case of the ultrasound diagnosis.

The display device 8, the input device 14, and the ultrasound probe 21 are connected to the ultrasound diagnostic apparatus main body 41 via the network NW, but in this case, the display device 8, the input device 14, and the ultrasound probe 21 may be connected to the network NW in a wired manner or in a wireless manner.

EXPLANATION OF REFERENCES 1, 1A, 1B: ultrasound diagnostic apparatus
2: transducer array
3: transmission circuit
4: reception circuit
5: transmission and reception circuit
6: image generation unit 7: display control unit
8: display device
9: image analysis unit
13: device control unit
14: input device
15: storage unit
21: ultrasound probe
22: processor
23: amplification unit
24: AD conversion unit
25: beam former
26: signal processing unit
27: DSC
28: image processing unit
31: highlighting unit
41: ultrasound diagnostic apparatus main body
B: blood vessel
C: insertion object
D: distance
NW: network
P: distal end
TH: distance threshold value
U: ultrasound image

What is claimed is:

1. An ultrasound diagnostic apparatus that displays an insertion object to be inserted into a blood vessel of a subject on an ultrasound image, the ultrasound diagnostic apparatus comprising:
a transducer array;
a transmission and reception circuit configured to
cause the transducer array to transmit an ultrasound beam toward the subject, and
process a reception signal output from the transducer array that has received an ultrasound echo from the subject to generate a sound ray signal;
a processor configured to
generate the ultrasound image based on the sound ray signal generated by the transmission and reception circuit,
detect the blood vessel and the insertion object by analyzing the ultrasound image, and
control the transmission and reception circuit such that a frame rate at which the ultrasound image is generated is adjusted, based on a relative positional relationship between the blood vessel and the insertion object which are detected.

2. The ultrasound diagnostic apparatus according to claim 1,
wherein the processor is further configured to control the transmission and reception circuit such that
the frame rate at which the ultrasound image is generated is set to a predetermined first rate when a distance between a distal end of the insertion object and the blood vessel which are detected exceeds a predetermined distance threshold value, and
the frame rate is switched to a second rate higher than the first rate when the distance between the distal end of the insertion object and the blood vessel which are detected is equal to or less than the predetermined distance threshold value.

3. The ultrasound diagnostic apparatus according to claim 2,
wherein the processor is further configured to control the transmission and reception circuit such that
the frame rate is set to a third rate when the distal end of the insertion object which is detected is inserted into the blood vessel and a displacement amount of the distal end of the insertion object in the blood vessel within a predetermined time is equal to or less than a displacement amount threshold value.

4. The ultrasound diagnostic apparatus according to claim 3,
wherein the third rate is a rate equal to the first rate or lower than the first rate.

5. The ultrasound diagnostic apparatus according to claim 4,
wherein the processor is further configured to control the transmission and reception circuit such that when the frame rate is the third rate, a resolution of the ultrasound image is higher than when the frame rate is the second rate.

6. The ultrasound diagnostic apparatus according to claim 3,
wherein the third rate is a rate equal to the second rate or higher than the second rate.

7. The ultrasound diagnostic apparatus according to claim 2,
wherein the processor is further configured to
measure any one of a diameter, a radius, a length of an outer circumference, or an area of the blood vessel which is detected, and
control the transmission and reception circuit such that the second rate becomes a higher rate as the diameter, the radius, the length of the outer circumference, or the area of the blood vessel is decreased.

8. The ultrasound diagnostic apparatus according to claim 3,
wherein the processor is further configured to
measure any one of a diameter, a radius, a length of an outer circumference, or an area of the blood vessel which is detected, and
control the transmission and reception circuit such that the second rate becomes a higher rate as the diameter, the radius, the length of the outer circumference, or the area of the blood vessel is decreased.

9. The ultrasound diagnostic apparatus according to claim 4,
wherein the processor is further configured to
measure any one of a diameter, a radius, a length of an outer circumference, or an area of the blood vessel which is detected, and
control the transmission and reception circuit such that the second rate becomes a higher rate as the diameter, the radius, the length of the outer circumference, or the area of the blood vessel is decreased.

10. The ultrasound diagnostic apparatus according to claim 5,
wherein the processor is further configured to
measure any one of a diameter, a radius, a length of an outer circumference, or an area of the blood vessel which is detected, and
control the transmission and reception circuit such that the second rate becomes a higher rate as the diameter, the radius, the length of the outer circumference, or the area of the blood vessel is decreased.

11. The ultrasound diagnostic apparatus according to claim 6,
wherein the processor is further configured to
measure any one of a diameter, a radius, a length of an outer circumference, or an area of the blood vessel which is detected, and
control the transmission and reception circuit such that the second rate becomes a higher rate as the diameter, the radius, the length of the outer circumference, or the area of the blood vessel is decreased.

12. The ultrasound diagnostic apparatus according to claim 2,
wherein the processor is further configured to
in the ultrasound image, detect a vein into which the insertion object is to be inserted as the blood vessel, and an artery together,
measure a distance between the vein and the artery, and
control the transmission and reception circuit such that the second rate becomes a higher rate as the distance between the vein and the artery is shorter.

13. The ultrasound diagnostic apparatus according to claim 3,
wherein the processor is further configured to
in the ultrasound image, detect a vein into which the insertion object is to be inserted as the blood vessel, and an artery together,
measure a distance between the vein and the artery, and
control the transmission and reception circuit such that the second rate becomes a higher rate as the distance between the vein and the artery is shorter.

14. The ultrasound diagnostic apparatus according to claim 4,
wherein the processor is further configured to
in the ultrasound image, detect a vein into which the insertion object is to be inserted as the blood vessel, and an artery together,
measure a distance between the vein and the artery, and
control the transmission and reception circuit such that the second rate becomes a higher rate as the distance between the vein and the artery is shorter.

15. The ultrasound diagnostic apparatus according to claim 5,
wherein the processor is further configured to
in the ultrasound image, detect a vein into which the insertion object is to be inserted as the blood vessel, and an artery together,
measure a distance between the vein and the artery, and
control the transmission and reception circuit such that the second rate becomes a higher rate as the distance between the vein and the artery is shorter.

16. The ultrasound diagnostic apparatus according to claim 6,
wherein the processor is further configured to
in the ultrasound image, detect a vein into which the insertion object is to be inserted as the blood vessel, and an artery together,
measure a distance between the vein and the artery, and
control the transmission and reception circuit such that the second rate becomes a higher rate as the distance between the vein and the artery is shorter.

17. The ultrasound diagnostic apparatus according to claim 7,
wherein the processor is further configured to
in the ultrasound image, detect a vein into which the insertion object is to be inserted as the blood vessel, and an artery together,
measure a distance between the vein and the artery, and
control the transmission and reception circuit such that the second rate becomes a higher rate as the distance between the vein and the artery is shorter.

18. The ultrasound diagnostic apparatus according to claim 1, further comprising:
a display device configured to display the ultrasound image generated by the processor;
wherein the processor is further configured to highlight the blood vessel and the insertion object which are detected, on the display device.

19. The ultrasound diagnostic apparatus according to claim 2, further comprising:
a display device configured to display the ultrasound image generated by the processor;
wherein the processor is further configured to highlight the blood vessel and the insertion object which are detected, on the display device.

20. A control method of an ultrasound diagnostic apparatus that displays an insertion object to be inserted into a blood vessel of a subject on an ultrasound image, the control method comprising:
causing a transducer array to transmit an ultrasound beam toward the subject, and processing a reception signal output from the transducer array that has received an ultrasound echo from the subject to generate a sound ray signal;
generating the ultrasound image based on the generated sound ray signal;
detecting the blood vessel and the insertion object by analyzing the generated ultrasound image; and
adjusting a frame rate at which the ultrasound image is generated, based on a relative positional relationship between the detected blood vessel and the detected insertion object.

* * * * *